United States Patent
Boroczky et al.

(10) Patent No.: US 11,170,900 B2
(45) Date of Patent: *Nov. 9, 2021

(54) METHOD AND APPARATUS FOR REFINING SIMILAR CASE SEARCH

(75) Inventors: Lilla Boroczky, Mount Kisco, NY (US); Lalitha Agnihotri, Hartsdale, NY (US); Luyin Zhao, Lawrenceville, NJ (US); Michael Chun-chieh Lee, Bronx, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

This patent is subject to a terminal disclaimer.

(21) Appl. No.: 12/747,615

(22) PCT Filed: Dec. 10, 2008

(86) PCT No.: PCT/IB2008/055204
§ 371 (c)(1),
(2), (4) Date: Sep. 21, 2010

(87) PCT Pub. No.: WO2009/083841
PCT Pub. Date: Jul. 9, 2009

(65) Prior Publication Data
US 2011/0022622 A1   Jan. 27, 2011

Related U.S. Application Data

(60) Provisional application No. 61/016,928, filed on Dec. 27, 2007.

(51) Int. Cl.
*G16H 50/70* (2018.01)
*G06F 16/532* (2019.01)
*G06F 16/535* (2019.01)

(52) U.S. Cl.
CPC ........... *G16H 50/70* (2018.01); *G06F 16/532* (2019.01); *G06F 16/535* (2019.01)

(58) Field of Classification Search
CPC .. G06F 19/3443; G06F 16/532; G06F 16/535; G06Q 50/24; G16H 50/00; G16H 50/20; G16H 50/70
(Continued)

(56) References Cited

U.S. PATENT DOCUMENTS 5,930,749 A * 7/1999 Maes .................. G10L 21/0272
                                                           704/219
7,136,852 B1 * 11/2006 Sterling ................ G06F 16/289
(Continued)

FOREIGN PATENT DOCUMENTS

JP        H11296533 A     10/1999
JP        2004287998 A    10/2004
(Continued)

OTHER PUBLICATIONS

Wikipedia, Mahalanobis distance, Dec. 11, 2007, accesased May 17, 2017 at https://en.Wikipedia.org/w/index.php?title=Mahalanobis_distance&oldid=177293670.*

(Continued)

*Primary Examiner* — William Spieler (57) ABSTRACT

The invention relates to search for cases in a database. According to the proposed method and apparatus, similarity matching is performed between an input case and a set of cases in an initial search to receive similar cases by using a given matching criterion. Then statistics on image and/or non-image-based features associated with the similar cases are calculated and presented to the user with the similar cases. In a search refinement the similar cases are refined by additional features that are determined by the user based on the statistics. The search refinement can be iterative depending on the user's need.

10 Claims, 3 Drawing Sheets

(58) Field of Classification Search
USPC .................................................. 707/748, 749
See application file for complete search history.

(56) References Cited

U.S. PATENT DOCUMENTS

| | | | | |
|---|---|---|---|---|
| 7,185,001 | B1* | 2/2007 | Burdick | G06F 16/345 |
| 7,272,593 | B1* | 9/2007 | Castelli et al. | 707/600 |
| 7,860,287 | B2* | 12/2010 | Zahlmann et al. | 382/128 |
| 2001/0003185 | A1* | 6/2001 | Lee | G06F 16/5838 |
| 2002/0138481 | A1* | 9/2002 | Aggarwal | G06Q 30/02 |
| 2003/0013951 | A1* | 1/2003 | Stefanescu | G16H 50/50 600/407 |
| 2003/0195883 | A1* | 10/2003 | Mojsilovic | G06K 9/46 |
| 2003/0216939 | A1* | 11/2003 | Bito | G06Q 50/22 705/2 |
| 2003/0225761 | A1* | 12/2003 | Wagener | G06F 16/9024 |
| 2005/0020903 | A1 | 1/2005 | Krishnan et al. | |
| 2005/0210015 | A1* | 9/2005 | Zhou | G06F 19/322 |
| 2006/0034508 | A1* | 2/2006 | Zhou | G06F 19/3443 382/156 |
| 2006/0189843 | A1* | 8/2006 | Nakamura | A61B 1/04 600/118 |
| 2006/0241978 | A1* | 10/2006 | Yoshii | G06Q 50/24 705/3 |
| 2007/0129991 | A1* | 6/2007 | Kuo | G16H 50/70 705/2 |
| 2007/0238065 | A1* | 10/2007 | Sherwood | G16H 50/50 433/24 |
| 2008/0027889 | A1* | 1/2008 | Zhou | G06F 19/00 706/50 |
| 2011/0022622 | A1 | 1/2011 | Boroczky et al. | |

FOREIGN PATENT DOCUMENTS

| | | |
|---|---|---|
| JP | 2007011604 A | 1/2007 |
| JP | 2007275440 A | 10/2007 |
| WO | 2005001740 A2 | 1/2005 |

OTHER PUBLICATIONS

Wikipedia, Euclidean distance, Dec. 21, 2007, accessed May 17, 2017 at https://en.Wikipedia.org/w/index.php?title=Euclidean_distance&oldid=179335558.*

Deserno, T. M., et al.; Extended Query Refinement for Medical Image Retrieval; 2008; Journal of Digital Imaging; 21(3)280-289.

Hung, S-Y., et al.; Mammographic case base applied for supporting image diagnosis of breast lesion; 2006; Expert Systems with Applications; 30:93-108.

Jurisica, I., et al.; Incremental Iterative Retrieval and Browsing for Efficient Conversational CBR Systems; 2000; Applied Intelligence; 12:251-268.

Muller, H., et al.; A review of content-based image retrieval systems in medical applications-clinical benefits and future directions; 2004; International Journal of Medical Informatics; 73:1-23.

* cited by examiner

Fig.1

Case in question

Age (year): 65
Smoking history (pack year): 15
Gender: Male
Other pulmonary diseases
    Emphysema: No
Cancer history: prostate 10 years ago
Lymph node: negative Statistics of retrieved cases Average age (year): 72 (Oldest = 90, Youngest = 32)
Smoking history (pack year): 20
Gender:  Male: 6    Female: 2
Other pulmonary diseases
Emphysema: 4 patients
Cancer history: no, primary lung
Lymph node: positive: 5, negative: 3

METHOD AND APPARATUS FOR REFINING SIMILAR CASE SEARCH

CROSS REFERENCE TO RELATED APPLICATIONS

This application claims the benefit of U.S. provisional application Ser. No. 61/016,928 filed Dec. 27, 2007 which is incorporated herein by reference.

FIELD OF THE INVENTION

The invention relates to searching, and more particularly, to a method and apparatus of hierarchical searching for case-based decision support in medical applications, for instance case-based computer-aided diagnosis and computer-aided therapy management.

BACKGROUND OF THE INVENTION

Case-based clinical decision support systems (CDSS) can assist physicians by identifying and presenting previous cases that have been diagnosed and treated, and are similar to the case under evaluation. These systems augment the traditional clinical decision making process, in which a physician's own recollection of previous or learned cases guides new clinical decisions. A case-based CDSS system will allow a physician to rapidly and reliably access a dataset that exceeds the historical experience possessed by any single physician.

Research has demonstrated the potential of case-based systems for computer-aided diagnosis (CADx) and computer-aided therapy management (CATM) to aid physicians in improving diagnosis and therapy. By retrieving cases in an inductive manner similar to the cognitive processes employed by experienced physicians, such systems are a natural fit for use in clinical circumstances. Therefore, case-based CADx systems will help physicians improve their diagnostic accuracy and reduce both unnecessary interventions and delays in treatment. In the CATM field, case-based systems could improve patient outcome and shorten treatment time by applying better treatment planning based on past similar cases.

Current case-based CDSS systems mostly present similar cases based on only image-based information and fail to incorporate patient medical history, which plays an important role in the diagnostic process. Often, they either present too many "similar" cases to the physician or the use of image-based information alone is insufficient to find truly clinically similar or relevant cases. Consequently, the case-based CDSS system can lose its original purpose. Instead of helping the physicians in their decision making process, their information overload is increased by being presented with too many cases, many of which are actually irrelevant. Additionally, image-based features may not be enough to find enough cases. This is particularly problematic if the case in question has an unusual visual appearance.

One possible way to solve this problem is to use image-based features and relevant non-image-based information, such as relevant previous or current diseases, lifestyle facts, genetic profiles, family medical history, patient's vital statistics, such as blood pressure, heart rate etc., associated with the patient in question. This additional non-image data can be combined with the image-based features to search for similar cases in a database. However, taking advantage of the prior art techniques in search, the retrieved results are based on a pre-determined criterion either fixed in the case-retrieval system or input in the beginning of the retrieval process. Therefore, such systems based on prior art cannot provide the physicians with chances to refine the search using their subjective sense of case similarity during the retrieving process, thus limiting the usefulness and efficiency of the case-retrieval. Moreover, because user input is limited during the search process, previously known systems lack transparency as to why certain cases are retrieved.

There is therefore a need to provide a searching method and apparatus that improve case-retrieval performance.

SUMMARY OF THE INVENTION

An object of the invention is to provide a method and apparatus of searching that improves case-retrieval performance when searching similar cases in a database. The present invention achieves this by proposing hierarchical searching methods and apparatus, in which search is performed using a multiple-step approach to retrieve similar cases for the user.

According to an aspect of the invention, the invention provides a method of searching cases in a database, said method comprising:
 a first step of performing similarity matching between an input case and cases in the database by using a first matching criterion, to identify a set of cases similar to said input case;
 calculating statistics on features associated with the set of similar cases;
 presenting the set of similar cases and the statistics to a user;
 receiving a user input including a second matching criterion based on said statistics; and
 a second step of performing similarity matching between the input case and the set of similar cases by using said second matching criterion.

The features associated with the set of similar cases are image-based and/or non-image based features. The first step of performing similarity matching is carried out as an initial search to identify cases similar to the input case. The second step of performing similarity matching is carried out as search refinement to refine the retrieval results in the initial search and this step can be repeated as many times as the user wishes.

By enabling similarity matching in a multiple-step approach driven by a user provided with statistics relevant to the case-retrieval result, this invention gives more insight to the user on how and why the particular similar cases are retrieved from a database than a one-step approach, resulting in improvement of the case-retrieval performance.

In an embodiment, when the cases in the database include a plurality of images classified according to different modalities, said first step of performing similarity matching comprising:
 performing similarity matching between an input case and cases in the database for each modality to identify a plurality of respective sets of similar cases by using said first matching criterion; and
 selecting cases that appear in at least two sets of said sets of similar cases, and to be used by said step of calculating statistics;
wherein said second step of performing similarity matching is performed between the input case and the selected similar cases.

In an embodiment, the first matching criterion includes at least one image-based feature and the second matching criterion includes at least one non-image-based feature. The similarity matching for an initial search is based on image-based features and the retrieval result is refined based on non-image features. Alternatively, the sequence of features used for the initial search and search refinement can be reversed, or the matching criteria may include both image and non-image-based features. In this way, the invention provides great flexibilities to the user.

It is advantageous that in the steps of performing similarity matching, the similarity value for each of the cases to be compared is calculated, thus indicating the degree of similarity between the input case and each of the retrieved cases. Furthermore, the result of search refinement in the consequent steps includes either moving cases entirely out from the set of similar cases or modulating the similarity rates for the set of similar cases based on the updated similarity matching criterion or a combination of both. In this way, the case-retrieval process fits better into the physician's decision-making process.

It is also advantageous that the user input further comprises an optional numerical importance value (weighting) given to any of the image or non-image-based features, with which the similarity matching is performed based on calculation of a similarity metric: for instance, Euclidean distance, Mahalanobis distance or Hamming distance. Alternatively the metric could be a weighted combination of these three.

It is also advantageous that user input may specify importance of features and acceptable ranges or values for those features. In this way, the user may specify directly that cases that do not adhere to these specifications should not be returned in the search results. Alternatively, the hierarchical search can be more conceptual, in which critical features may be identified in the user input but ranges of feature values are not specified. The physician may specify the different features to use, for example to retrieve cases with similar therapy and so on, or refine the search based on diagnosis outcome of the patient in question. This is especially helpful for case-based computer-assisted treatment planning.

According to another aspect, the invention provides an apparatus of searching to retrieve cases in a database, said apparatus comprising:

a first matching unit for performing similarity matching between an input case and cases in the database by using a first matching criterion, to identify a set of cases similar to said input case;

a calculating unit for calculating statistics on features associated with the set of similar cases;

a presenting unit for presenting the set of similar cases and the statistics to a user;

a receiving unit for receiving a user input including a second matching criterion based on said statistics; and a second matching unit for performing similarity matching between the input case and the set of similar cases by using said second matching criterion.

In an embodiment, the cases in the database include a plurality of images acquired using different imaging modalities, wherein the first matching unit is further arranged for performing similarity matching between an input case and cases in the database for each modality to identify a plurality of respective sets of similar cases by using said first matching criterion and selecting cases that appear in at least two sets of said sets of similar cases, and to be used by said step of calculating statistics; and the second matching unit is further arranged for performing similarity matching between the input case and the selected similar cases In a further embodiment, the apparatus 300 comprises a controller 360 for controlling an iterative step of performing similarity matching between the input case and an updated set of similar cases by using an updated similarity matching criterion based on a further user input to retrieve cases similar to the user.

Modifications and variations thereof, of the inventions defined in independent claims, which correspond to modifications of the method and apparatus and variations thereof, being described, can be carried out by a skilled person on basis of the present description.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
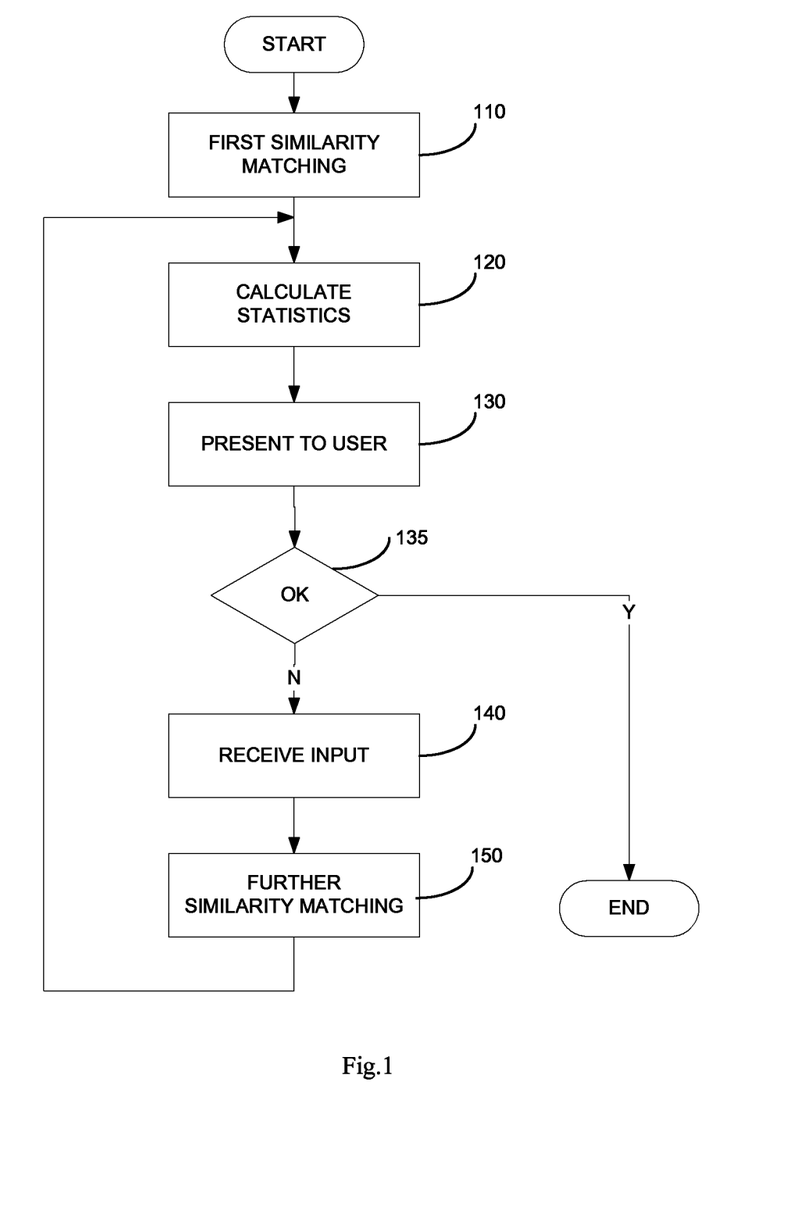
FIG. 1 is a flowchart showing an exemplary embodiment of a method in accordance with the invention.

FIG. 1 is a flowchart showing an exemplary embodiment of a method, in accordance with the invention, for retrieving cases from a database.

Referring to FIG. 1, the process of the method starts from a first step 110 of performing similarity matching between an input case and cases in the database by using a first matching criterion, to identify a set of cases similar to said input case. This step is carried out as an initial search for retrieving cases from the database.

The first matching criterion used for similarity matching may include image-based features, which are derived from images of a medical subject. These features may include, for instance, shape of a tumor, texture of the tumor, and size change of the tumor due to treatment in case scans over time, etc. Alternatively, the first matching criterion may include non-image-based features, which are derived from clinical information, for instance relevant previous or current diseases, lifestyle facts, genetic profiles, and family medical history. The clinical information may be extended to include a physician's particular knowledge/information of the patient to be diagnosed or treated, for instance weight, allergies, and other vital statistics, etc.

In an embodiment, when the cases in the database include a plurality of images classified according to different modalities, for example PET and CT scans in case of lung cancer, said first step 110 of performing similarity matching may comprises a sub-step of performing similarity matching between an input case and cases in the database for each modality to identify a plurality of respective sets of similar cases by using said first matching criterion; and a sub-step of selecting cases that appear in at least two sets of said sets of similar cases. The selected similar cases are intended to be used by subsequent steps of calculating statistics that will be described later.

It is advantageous that the similarity values for all cases to be compared are computed for indicating the degree of similarity between the input case and the case to be compared. The similarity values are helpful for physicians to evaluate the retrieval results, because case similarity lies on a continuum, ranging from cases that are practically identical to those that do not resemble each other at all.

The method further comprises a step 120 of calculating statistics on image-based and/or non-image-based features associated with the set of similar cases retrieved in the first step search, e.g. in the step 110. In case the cases in the database include a plurality of images classified according to different modalities (e.g. PET, CT, etc), the statistics are calculated on features associated with the selected similar cases that appear in two or more modalities.

In an embodiment, when the similar cases are retrieved from the database based on image-based features, the statistics on non-image-based features associated with the set of similar cases are calculated. The statistics describe non image-based information, such as clinical information, which is available in the database and may be relevant to the case in question, for example, the number of males or females in the retrieved similar cases, smoking history (e.g. in number of years) for lung cancer diagnosis, cancer history in the female line of the family for breast cancer diagnosis (e.g. number of relatives previously diagnosed with cancer).

Alternatively, when the similar cases are retrieved from the database based on non-image-based features, the statistics on image-based features associated with the set of similar cases are calculated. The statistics describe image-based information, such as the average size of the tumor or the number or percent of cases with a size larger than a predefined threshold.

It is also possible in this step that the statistics on both image-based features and non-image-based features are calculated, no matter which type of features are used to retrieve the similar cases. The physician may use the statistics for formulating subsequent inputs (detailed in the following), selecting additional features for refining the search, and even adjusting searching strategy.

The method further comprises a step 130 of presenting the set of similar cases and the statistics to a user. There are different ways to present the similar cases and the statistics to a user in a meaningful manner, for example, outputting the information to a screen to display.

It is advantageous to present the similarity values for each identified similar cases to the user when the similarity values are calculated in the step 110. Furthermore, the physician may be advised as to how many cases are actually being processed and how many are being presented.

Figure 2:
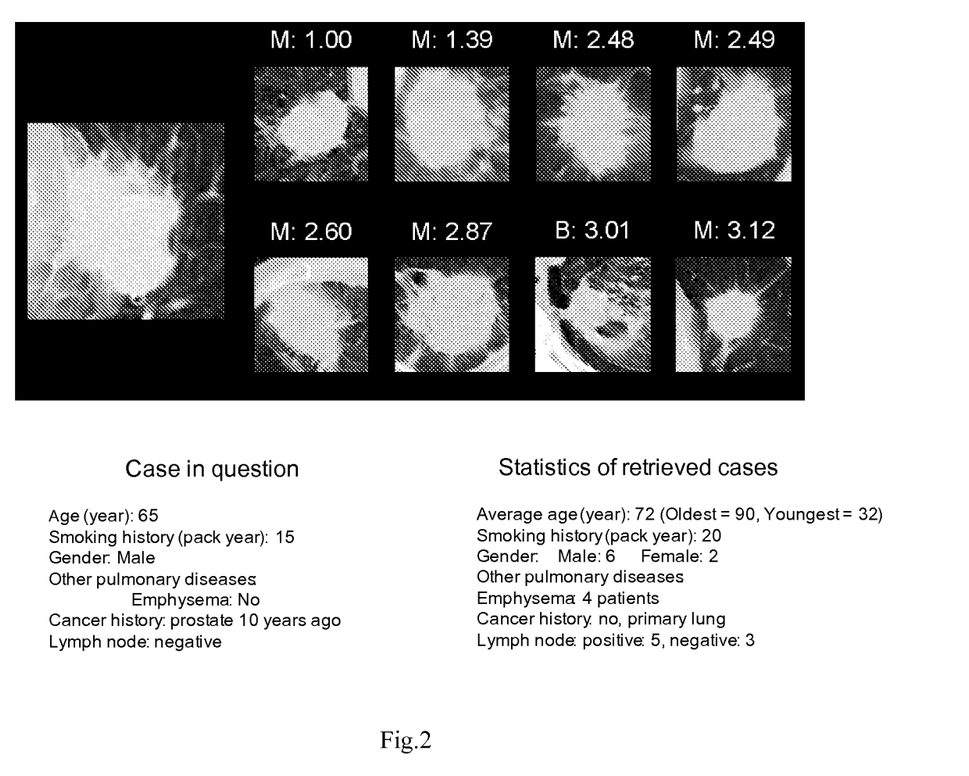
FIG. 2 shows an exemplary output of an initial search for lung cancer diagnosis using only multi-slice CT scans.

FIG. 2 gives an exemplary output after the step 110 of similarity matching for lung cancer diagnosis using only multi-slice CT scans. In the screen shown in FIG. 2, the upper-left part represents an image of an input case, and the lower-left part represents the available clinical information for this case including the age, smoking history, gender, other pulmonary diseases, for instance emphysema, cancer history, and lymph node status.

On the upper-right part of the screen, eight similar images are shown, that are retrieved from the database of prior cases with known diagnosis. On the top of each retrieved images, there are indications of the diagnostic outcome of the case, e.g. malignant or benign and the similarity distance between the input case and each case retrieved by step 110. For example, "M: 1.39" on the top of the second image in the first row indicates the diagnostic outcome for the case is malignant and the similarity distance between the case and the case in question is 1.39. The similarity distance calculation may correspond to a Euclidean distance computed based on features representing the cases (distance computation will be detailed in the following). The smaller the number, the more similar the retrieved case to the input case.

On the lower-right part of the screen the statistics are shown associated with the retrieved cases that include clinical information (i.e. non image-based information that relate to each retrieved similar cases), such as average age, smoking history, gender distribution, how many have been diagnosed with other diseases (e.g. emphysema, cancer history and the number of cases with positive or negative lymph node, etc).

By viewing the retrieved similar cases and the statistics, the physician may decide if he/she wants to perform the subsequent search for refinement. The number of similar cases identified in the first step of search may be small, and further refinement may not be necessary. A more likely scenario is that the number of similar cases may be very large, and the physician may then decide to perform a subsequent search for refinement. In such a situation, the physician formulates a user input including additional features, based on his/her personal perception regarding the similarity and the analysis of the statistics, for refining or constraining the similarity matching criterion.

The method thus further comprises a step 135 of deciding whether search refinement is needed. In case the physician is satisfied with the retrieval result after a number of refinements search, the process stops (END), otherwise the refinement is activated as explained in the following.

The method further comprises a step 140 of receiving a user input including a second matching criterion based on said statistics. The second matching criterion includes additional features that are different from the features in the first matching criterion. For example, when the first matching criterion includes image-based features, the second matching criterion may include non-image-based features, depending on the physician's perception of the retrieved similar cases and the information described by the statistics. Alternatively, the physician may reverse the sequence of the first and second similarity matching criteria.

In an embodiment, the method allows the physician to select from a menu of the relevant features, drag and drop icons representing relevant features, use a series of sliders, menus, and toggle switches to rate features according to their importance, or enter free form or structured text. Furthermore, the method may allow the physician to save common input including sample cases and features for similarity matching, and to choose from his/her own pool of saved inputs. In some applications, the method allows these inputs to be read and analyzed by payers, for instance the relevant insurer, or hospital administrators to monitor physician performance.

In practical applications, the physician may adjust his/her searching criterion and even search strategy based on his/her perception of the similar cases and the statistics information. For example, for lung cancer diagnosis, it could be important to closely consider the patient's history with respect to other pulmonary diseases such as emphysema or have a cancer history. Furthermore, other lifestyle information may also be relevant. For example, if the patient has worked for 15 years as a flight attendant 10 years ago, he/she was exposed to significant amounts of second-hand smoke. Thus, if the database has information on second-hand smoke status of the patient, the physician can reverse the similarity matching criteria. In this case, he/she may like to search the database for patients with second-hand smoke exposure, e.g., to perform similarity matching using a non-image-based feature to prescreen the set of cases, and then to refine the search based on image-based features of the lung nodule.

Alternatively, it could be that from the retrieved cases, the physician selects one or two cases that are very similar and then the second similar matching criterion may include image-based features and non-image-based features, e.g. clinical information based on these selected cases. The physician may also specify the different features to use, for example to retrieve cases with similar therapy and so on, or refine the search based on diagnostic outcome of the patient in question. This is especially helpful for case-based computer-assisted treatment planning.

The method further comprises a second step 150 of performing similarity matching between the input case and the selected similar cases by using said second matching criterion, to refine the retrieval result. If the cases in the database include a plurality of images classified according to different modalities, the second step of similarity matching is performed between the input case and a particular set of similar cases or each set of similar cases that includes the selected similar cases used for statistics calculation.

Once the retrieval result is refined by the step 150, the statistics on the features associated with the refined set of similar cases are calculated by repeating step 120 and presented to the physician with the refined set of similar cases by repeating step 130. Similarly as explained before, the physician views and evaluates the retrieved result and determines whether further search refinement is needed. When further search refinement is needed, the step 135, 140, 150 will be repeated for obtaining an updated set of similar cases by using an updated similarity matching criterion based on a further user input.

The search refinement or iterations can be repeated as many times as needed. The physician can remove intermediate refinement steps or store them for later use. However, in practice, the steps for search refinement are expected to be performed only a few times, otherwise it might decrease the diagnosis efficiency of the physicians. The number of refinement iterations is likely to depend on the experience of the physician. For this reason, the method may be used also for physician training, in addition to clinical decision support.

The similarity matching performed in the first and second or subsequent steps of similarity matching can be based directly on the physician request, for example, "show only patients between 30-35 years old at diagnosis". In this case, specific numerical criteria are provided, and the similarity matching for search may proceed via exclusion or inclusion with simple Boolean logic.

Alternatively, the similarity matching can be more conceptual, in which case-characteristics, e.g. non-image-based features associated with the cases, are given but ranges of values are not specified, for example "account for age and smoking history". In this approach, the case-characteristics can be ranked in terms of importance or given a numerical importance value by the physician and then more general mathematical similarity matching can be used for searching similar cases.

The similarity matching can be done using well-known similarity metrics, for example Euclidean distance, which is defined as the straight-line distance between two points $p=(p_1,p_2,\ldots,p_N)$ and $q=(q_1,q_2,\ldots,q_N)$, e.g., $$d = \sqrt{\sum_{i=1}^{N} (p_i - q_i)^2},$$

wherein $p=(p_1,p_2,\ldots,p_N)$ denotes a set of numerical values representing features (image-based features and/or non-image-based features) of the input case, $q=(q_1,q_2,\ldots,q_N)$ denotes a set of numerical values representing features of a case in the database to be searched, and N denotes the number of features requested by the physician for similarity matching. The Euclidean distance d represents the similarity distance between the input case and the compared case, and the smaller the distance the more similar the retrieved case to the case in question.

The similarity matching may alternatively use other well-known similarity metrics, such as Mahalanobis distance. By expressing the two cases as vectors $\vec{x}$ and $\vec{y}$ covariance of the population expressed in the covariance matrix $\Sigma$, the distance can be expressed as $d(\vec{x},\vec{y}) = \sqrt{(\vec{x}-\vec{y})^T \Sigma_{-1} (\vec{x}-\vec{y})}$.

Other similar metrics or a weighted combination of those described above may be used for similarity matching depending on practical applications. In case the set of features are represented in binary strings, the Hamming distance, which indicates the number of bits that differ between two binary strings, may be used to compute the similarity distance between two cases.

The results of search refinement in the second, or subsequent steps of performing similarity matching could be performed by moving cases entirely out from the retrieved set of similar cases or modulating the similarity values for each retrieved similar case in order to more closely match the user's desired output. The refinement can be performed sequentially based on only one non-image-based feature each time or can be also performed simultaneously using multiple non image-based features together. Further, the retrieval result could be refined using image-based features as done in the first step of search.

The search refinement step may be iterated for a number of times depending on the physician's need. For each refinement, the physician is advised via graphical display on statistics information on the search results. Furthermore, the physician may specify the different features to use, for example, to refine the search with similar therapy or the diagnosis outcome of the patient in question.

The above method as illustrated in FIG. 1 can be implemented with software or hardware, or in combination of both.

Figure 3:
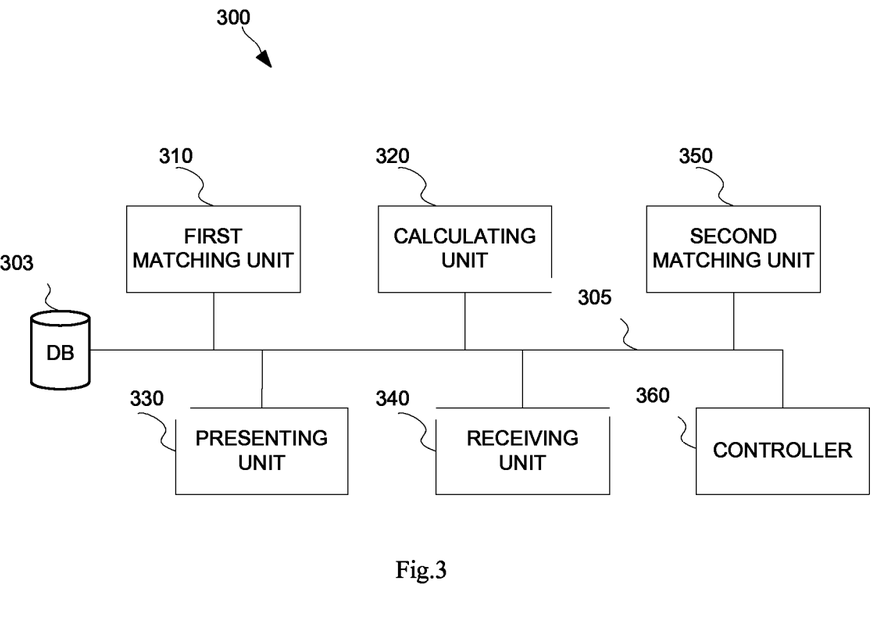
FIG. 3 is a block diagram showing an exemplary embodiment of an apparatus in accordance with the invention.

FIG. 3 is a block diagram showing an exemplary embodiment of an apparatus 300 in accordance with the invention. According to the invention, the apparatus 300 comprises a first matching unit 310 for performing similarity matching between an input case and cases in the database by using a first matching criterion, to identify a set of cases similar to said input case. The first matching unit 310 is intended to carry out the step 110 in the method.

The apparatus 300 further comprises a calculating unit 320 for calculating statistics on image-based and/or non-image-based features associated with the set of similar cases. The calculating unit 320 is intended to carry out the step 120 in the method.

The apparatus 300 further comprises a presenting unit 330 for presenting the set of similar cases and the statistics to a user. The presenting unit 330 is intended to carry out step 130 in the method.

The apparatus 300 further comprises a receiving unit 340 for receiving a user input including a second matching criterion based on said statistics. The receiving unit 340 is intended to carry out the step 140 in the method.

The apparatus 300 further comprises a second matching unit 350 for performing similarity matching between the input case and the set of similar cases by using said second matching criterion. The second matching unit 350 is intended to carry out the step 150 in the method.

In an embodiment, in case that the cases in the database include a plurality of images classified according to different modalities, wherein the first matching unit 310 is further arranged for performing similarity matching between an input case and cases in the database for each modality to identify a plurality of respective sets of similar cases by using said first matching criterion and selecting cases that appear in at least two sets of said sets of similar cases, and to be used by said step of calculating statistics; and the second matching unit 350 is further arranged for performing similarity matching between the input case and the selected similar cases.

The apparatus 300 may also comprise a database 303 including cases for retrieval and an internal bus 305 for collecting the units in the apparatus 300. Furthermore, the apparatus 300 comprises a controller for controlling an iterative step of performing similarity matching between the input case and an updated set of similar cases by using an updated similarity matching criterion based on a further user input to retrieve cases similar to the user.

In an embodiment, the first and/or second matching units 310 and 350 may further arranged for calculating a similarity value for each case to be compared, for indicating the degree of similarity between the input case and the case to be compared.

The invention may be integrated into radiology informatics or healthcare informatics products as a feature or as a separate add-on module. The invention may also be implemented as a stand-alone case-based CADx or therapy management workstation product or a combination of both. The invention can be used for a computer-aided diagnosis system in conjunction with one or more diagnostic or monitoring modalities. The invention may be used for assisting diagnosis of different diseases, for confirming suspected diagnoses during the diagnostic process and for assisting treatment planning by physicians. Other applications include teaching, emergency diagnosis and case-based computer aided therapy management.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by unit of hardware comprising several distinct elements and by unit of a programmed computer. In the apparatus claims enumerating several units, several of these units can be embodied by one and the same item of hardware or software. The usage of the words first, second and third, et cetera, does not indicate any ordering. These words are to be interpreted as names.

The invention claimed is:

1. A method of searching cases in a database, said method comprising:
a first step of performing similarity matching between an input case and cases in the database by using a first matching criterion that includes at least one image-based feature to identify a set of cases similar to said input case, the at least one image-based feature including at least one of shape of a tumor in an image, texture of the tumor, and size change of the tumor, the cases in the database including a plurality of images classified according to different imaging modalities, the first step of similarity matching between an input case and cases in the database being performed for each imaging modality to identify a plurality of respective sets of similar cases by using said first matching criterion;
calculating statistics on features associated with the set of similar cases, wherein the statistics describe non-image-based clinical information;
presenting the set of similar cases and the statistics to a user;
receiving a user input including a second matching criterion that includes at least one non-image-based feature that is derived from clinical information and based on said statistics, the clinical information including at least one of relevant previous or current diseases, lifestyle facts, genetic profiles, family medical history, a physician's particular knowledge and information of a patient to be diagnosed or treated, weight, allergies, and vital statistics;
a second step of performing similarity matching between the input case and the set of similar cases by using said second matching criterion to generate a refined search result; and
displaying the set of similar cases;
wherein the features associated with the set of similar cases comprise image-based features and non-image based features; and
wherein the user input further comprises a numerical value given to each feature in the second criterion, and the second step of performing similarity matching includes calculating a similarity metric by using the numerical values; and
wherein the steps of performing similarity matching include calculating a similarity value for each case to be compared, for indicating the degree of similarity between the input case and the case to be compared, the similarity value being a weighted combination of a Euclidean distance and Mahalanobis distance;
wherein the second step and generating the refined search result are performed iteratively and further comprise modulating similarity rates for the set of similar cases based on an updated similarity matching criterion, and based on the at least one non-image-based feature; and
displaying to the user one or more images associated with one or more retrieved similar cases, and graphically overlaying on each image information indicative of a diagnostic outcome of the respective retrieved similar case and the calculated similarity value between the retrieved similar case and the input case.

2. A method as claimed in claim 1, wherein, said first step of performing similarity matching comprising:
selecting cases that appear in at least two sets of said sets of similar cases, and to be used by said step of calculating statistics;
wherein said second step of performing similarity matching is performed between the input case and the selected similar cases.

3. A method as claimed in claim 1, further comprising an iterative step of performing similarity matching between the input case and an updated set of similar cases by using an updated similarity matching criterion based on a further user input to retrieve cases similar to the user.

4. A method as claimed in 1, wherein the user input further comprises any one of image-based features and non-image-based features presented in the similar cases that are the most similar cases to the input case.

5. An apparatus for searching cases in a database, said apparatus comprising:
- a non-transitory computer-readable medium that stores computer-executable instructions comprising:
  - a first matching unit for performing similarity matching between an input case and cases in a database by using a first matching criterion that includes at least one image-based feature, to identify a set of cases similar to said input case; the cases in the database including a plurality of images classified according to different imaging modalities,
  - a calculating unit for calculating statistics on features associated with the set of similar cases, wherein the statistics describe non-image-based clinical information;
  - a presenting unit for presenting the set of similar cases and the statistics to a user;
  - a receiving unit for receiving a user input including a second matching criterion that includes at least one non-image-based feature that is derived from clinical information and based on said statistics;
  - a second matching unit for performing similarity matching between the input case and the set of similar cases by using said second matching criterion to generate a refined search result; and
  - a display configured to display the set of similar cases;
- wherein the features associated with the set of similar cases comprise image-based features and non-image based features; and
- wherein the user input further comprises a numerical value given to each feature in the criterion, and the second step of performing similarity matching includes calculating a similarity metric by using the numerical values;
- wherein the second step and generating the refined search result are performed iteratively and further comprise modulating similarity rates for the set of similar cases based on an updated similarity matching criterion, and based on the at least one non-image-based feature; and
- wherein the display is further configured to display to the user one or more images associated with one or more retrieved similar cases, and graphically overlay on each image information indicative of a diagnostic outcome of the respective retrieved similar case and the calculated similarity value between the retrieved similar case and the input case.

6. An apparatus as claimed in claim 5, wherein the first matching unit is further arranged for performing similarity matching between an input case and cases in the database for each imaging modality to identify a plurality of respective sets of similar cases by using said first matching criterion and selecting cases that appear in at least two sets of said sets of similar cases, and to be used by said step of calculating statistics; and the second matching unit is further arranged for performing similarity matching between the input case and the selected similar cases.

7. An apparatus as claimed in claim 5, wherein the features associated with the set of similar cases are image-based and/or non-image based features.

8. An apparatus as claimed in claim 7, wherein any one of the first and second matching units is further arranged for calculating a similarity value for each case to be compared, for indicating the degree of similarity between the input case and the case to be compared.

9. An apparatus as claimed in claim 5 further comprising a controller for controlling an iterative step of performing similarity matching between the input case and an updated set of similar cases by using an updated similarity matching criterion based on a further user input to retrieve cases similar to the user.

10. A method of searching cases in a database, said method comprising:
- a first step of performing similarity matching between an input case and cases in the database by using a first matching criterion that includes at least one non-image-based feature that is derived from clinical information, to identify a set of cases similar to said input case, the cases in the database including a plurality of images classified according to different imaging modalities, the first step of similarity matching between an input case and cases in the database being performed for each imaging modality to identify a plurality of respective sets of similar cases;
- calculating statistics on features associated with the set of similar cases, wherein the statistics describe non-image-based clinical information;
- presenting the set of similar cases and the statistics to a user;
- receiving a user input including a second matching criterion that includes at least one image-based feature and is based on said statistics; and
- a second step of performing similarity matching between the input case and the set of similar cases by using said second matching criterion to generate a refined search result;
- displaying the set of similar cases;
- wherein the features associated with the set of similar cases comprise image-based features and non-image based features; and
- wherein the user input further comprises a numerical value given to each feature in the criterion, and the second step of performing similarity matching includes calculating a similarity metric by using the numerical values;
- wherein the second step and generating the refined search result are performed iteratively and further comprise modulating similarity rates for the set of similar cases based on an updated similarity matching criterion, and based on the at least one non-image-based feature; and
- displaying to the user one or more images associated with one or more retrieved similar cases, and graphically overlaying on each image information indicative of a diagnostic outcome of the respective retrieved similar case and the calculated similarity value between the retrieved similar case and the input case.

* * * * *